(12) United States Patent
Hansegård et al.

(10) Patent No.: US 8,795,178 B2
(45) Date of Patent: Aug. 5, 2014

(54) ULTRASOUND IMAGING SYSTEM AND METHOD FOR IDENTIFYING DATA FROM A SHADOW REGION

(71) Applicant: General Electric Company, Schenectady, NY (US)

(72) Inventors: Jøger Hansegård, Oslo (NO); Erik N. Steen, Moss (NO)

(73) Assignee: General Electric Company, Schenectady, NY (US)

( * ) Notice: Subject to any disclaimer, the term of this patent is extended or adjusted under 35 U.S.C. 154(b) by 101 days.

(21) Appl. No.: 13/731,531

(22) Filed: Dec. 31, 2012

(65) Prior Publication Data

US 2014/0187947 A1    Jul. 3, 2014

(51) Int. Cl.
*A61B 8/00* (2006.01)
*A61B 8/08* (2006.01)

(52) U.S. Cl.
CPC . *A61B 8/52* (2013.01); *A61B 8/461* (2013.01); *A61B 8/483* (2013.01)
USPC .......................................... 600/439; 600/440

(58) Field of Classification Search
CPC .......... A61B 8/00; A61B 8/463; A61B 8/5269
USPC .................................................. 600/440, 439
See application file for complete search history.

(56) References Cited

U.S. PATENT DOCUMENTS

| 7,104,957 B2 | 9/2006 | Miller |
| 2005/0113695 A1 * | 5/2005 | Miller .......................... 600/443 |
| 2007/0276243 A1 | 11/2007 | Gerard et al. |

* cited by examiner

*Primary Examiner* — Unsu Jung
*Assistant Examiner* — Rajeev Siripurapu

(57) ABSTRACT

An ultrasound imaging system and method includes acquiring ultrasound data of a region-of-interest including an interventional device with a probe, identifying a position of the interventional device with respect to the probe, and identifying a shadow region within the region-of-interest based on the position of the interventional device. The system and method includes identifying a subset of the ultrasound data acquired from the shadow region, generating an image including a graphical indicator identifying a shadow region area generated from the subset of the ultrasound data, and displaying the image.

21 Claims, 5 Drawing Sheets

ULTRASOUND IMAGING SYSTEM AND METHOD FOR IDENTIFYING DATA FROM A SHADOW REGION

FIELD OF THE INVENTION

This disclosure relates generally to an ultrasound imaging system and method for visually identifying or distinguishing a portion of an image generated based on data acquired from a shadow region.

BACKGROUND OF THE INVENTION

Ultrasound-guided interventional procedures typically rely on ultrasound images for real-time position data of an interventional device, such as a catheter, or an implantable device, such as a stent, in order to properly position and orient the interventional device. However, the presence of the interventional device may create a shadow region that has an undesirable effect on the ultrasound image used by a clinician to guide the interventional device. The interventional device may scatter or reflect much of the acoustic energy used to generate the image, thus making it difficult or impossible to accurately visualize structure in the portion of the image based on data acquired from the shadow region. Due to the scattering and reflection caused by the interventional device, it may be difficult to determine if a portion of the image is generated from reliable data acquired from outside the shadow region or from unreliable data acquired from the shadow region. This may be even more problematic when viewing arbitrary cut-planes or volume renderings generated from 3D or 4D data due to the added difficulty of remaining oriented with respect to the original acquisition geometry.

For these and other reasons an improved method and ultrasound imaging system for identifying data acquired from a shadow region is desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring ultrasound data with a probe of a region-of-interest, the region-of-interest including an interventional device. The method including automatically identifying a position of the interventional device with respect to the probe and automatically identifying within the region-of-interest a shadow region based on the position of the interventional device with respect to the probe. The method includes automatically identifying a first subset of the ultrasound data that was acquired from the shadow region. The method includes generating an image based on the ultrasound data, the image including a graphical indicator identifying a shadow image area generated from the first subset of the ultrasound data and displaying the image.

In an embodiment, a method of ultrasound imaging includes acquiring ultrasound data with a probe of a region-of-interest, the region of interest including an interventional device. The method includes automatically identifying a position of the interventional device with respect to the probe. The method includes automatically identifying within the region-of-interest a shadow region and a non-shadow region based on the position of the interventional device with respect to the probe and automatically identifying a first subset of the ultrasound data that was acquired from the shadow region and a second subset of the ultrasound data that was acquired from the non-shadow region. The method includes visualizing the first subset of the ultrasound data differently than the second subset of the ultrasound imaging data to generate an image and displaying the image.

In another embodiment, an ultrasound imaging system includes a probe, a display device, and a processor in electronic communication with the probe and the display device. The processor is configured to control the probe to acquire ultrasound data of a region-of-interest including an interventional device. The processor is configured to identify a position of the interventional device with respect to the probe and identify a shadow region in the region-of-interest caused by the interventional device based on the position of the interventional device with respect to the probe. The processor is configured to identify a non-shadow region in the region of interest and identify a first subset of the ultrasound data that was acquired from the shadow region and a second subset of the ultrasound data that was acquired from the non-shadow region. The processor is configured to generate an image by visualizing the first subset of the ultrasound data differently than the second subset of the ultrasound data and display the image on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
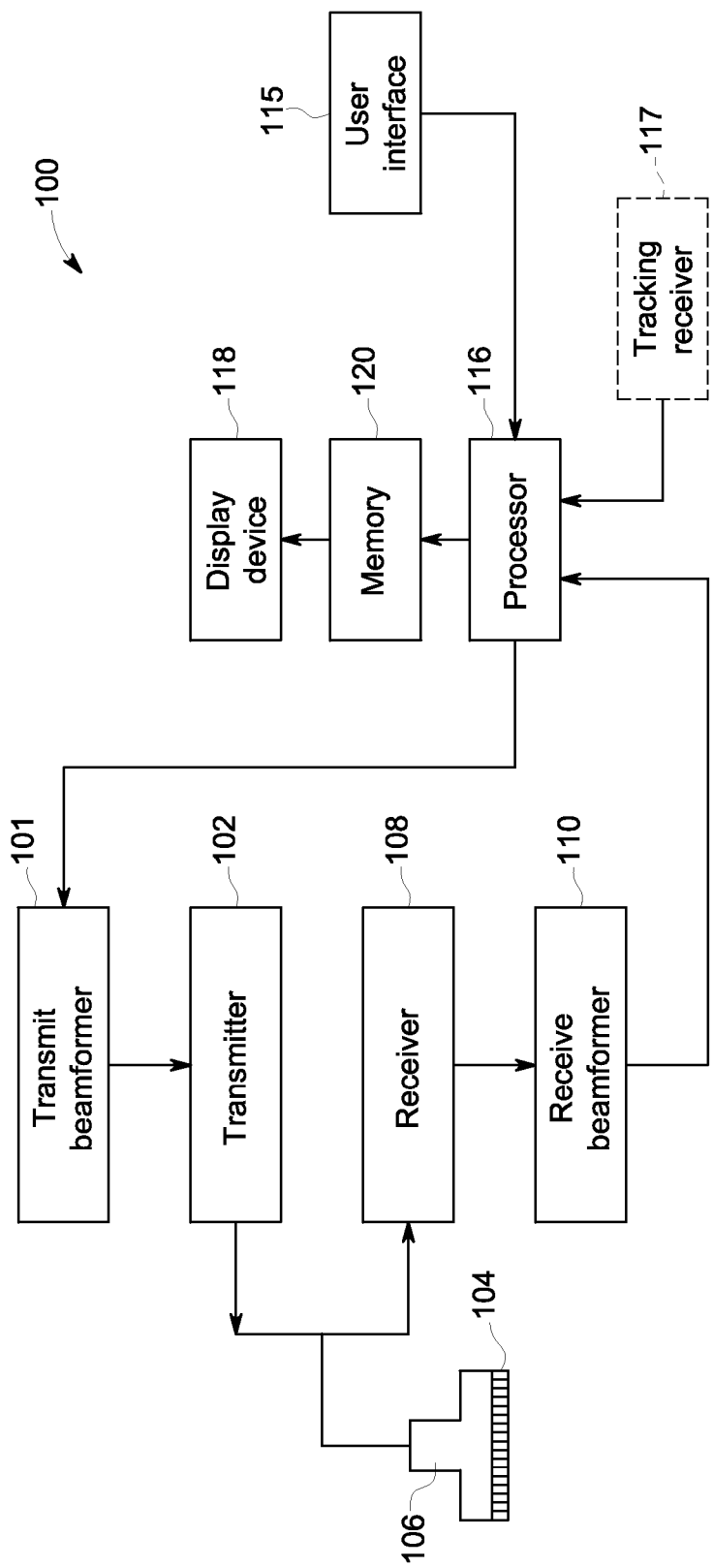
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). The probe 106 may be a 2D array probe according to an embodiment. However, any other type of probe may be used according to other embodiments. The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes a processor 116 to control the transmit beamformer 101, the transmitter 102, the receiver 108 and the receive beamformer 110. The processor 116 is in electronic communication with the probe 106. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire and display data a real-time volume-rate of 7-20 volumes/sec. However, it should be understood that the real-time frame rate may be dependent on the length of time that it takes to acquire each volume of data. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a frame-rate of, for example, 10 Hz to 30 Hz. Images generated from the data may be refreshed at a similar frame-rate. Other embodiments may acquire and display data at different rates. For example, some embodiments may acquire data at a frame-rate of less than 10 Hz or greater than 30 Hz depending on the size of the data and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium. The ultrasound imaging system may optionally include a tracking receiver 117. The tracking receiver 117 is configured to receive signals from a tracking device that may be optionally attached to an interventional device.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
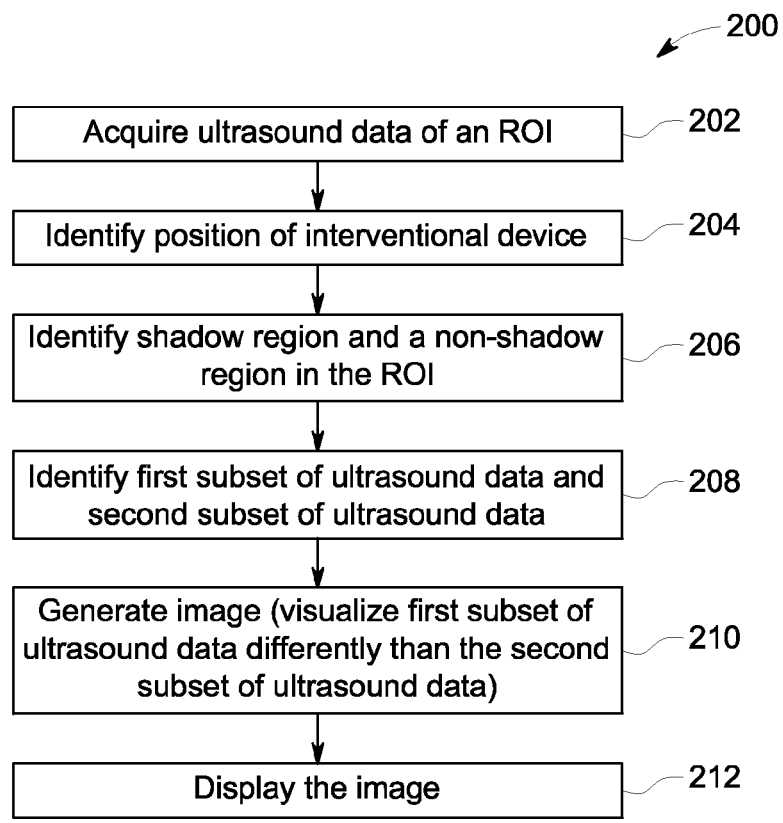
FIG. 2 is a flow chart of a method in accordance with an embodiment.

FIG. 2 is a flow chart of a method in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the identification of a shadow region and a non-shadow region in an ROI and the display of an image where ultrasound data acquired from the shadow region is visualized differently than the ultrasound data acquired from the non-shadow region. The method 200 will be described according to an exemplary embodiment where the method 200 is implemented by the processor 116 of the ultrasound imaging system 100 of FIG. 1.

Figure 3:
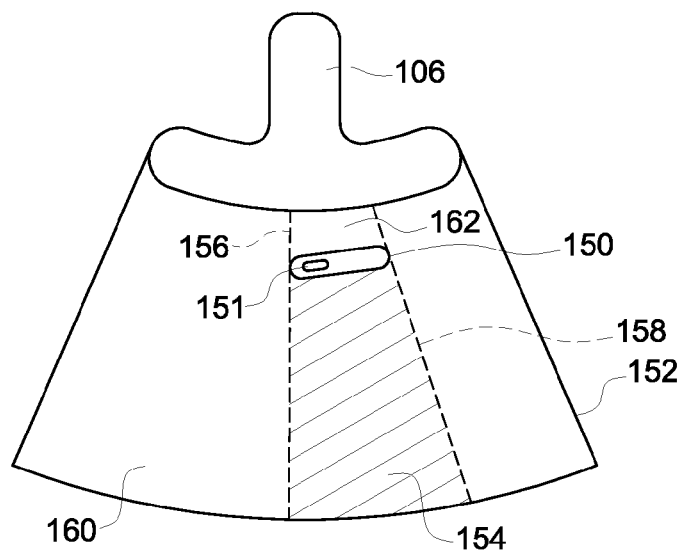
FIG. 3 is a schematic representation of an interventional device in accordance with an embodiment.

FIG. 3 is a schematic representation of the probe 106 and an interventional device 150 according to an exemplary embodiment. A tracking device 151 may optionally be attached to the catheter according to some embodiments. The tracking device 151 will be described in detail hereinafter. A region-of-interest (ROI) 152 is also shown with respect to the probe 106 and the interventional device 150. The probe 106 may be a sector probe according to the embodiment shown in FIG. 3, but it should be appreciated that other embodiments may use probes of different types including a linear array probe, a curved linear array probe, a mechanical 3D probe, a 2D matrix array probe, or any other type of ultrasound probe. The ROI 152 is fan-shaped due to the geometry of the probe 106. According to other embodiments, the clinician may select an ROI that is just a portion of the total field-of-view of the probe 106. For example, the clinician may select an ROI that is a subset of the ROI 152 shown in FIG. 3.

Figure 4:
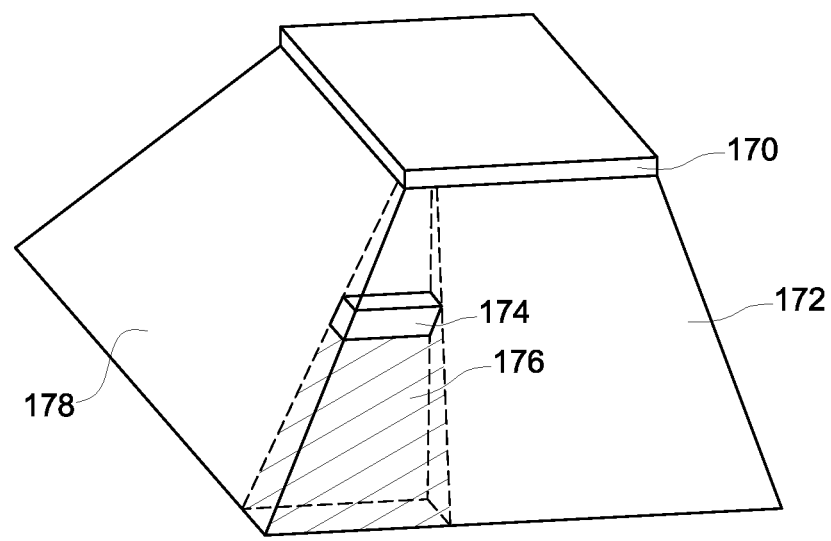
FIG. 4 is a schematic representation of a 2D array and a region-of-interest (ROI) in accordance with an embodiment.

FIG. 4 is a schematic representation of a 2D array 170 and a region-of-interest (ROI) 172 in accordance with an embodiment. The ROI 172 is a 3D ROI, and the 2D array 170 may be a component of a probe (not shown in FIG. 4). A 3D ROI such as the 3D ROI 172 could also be acquired by a mechanical probe or by using a 2D probe to acquire a volume of data. An interventional device 174 is shown within the 3D ROI 172. A shadow region 176 is positioned on the distal side of the interventional device 174. It should be appreciated that the shadow region 176 is a volume in accordance with an embodiment. A non-shadow region 178 includes all of the ROI except for the shadow region 176. Those skilled in the art will appreciate that the size and position of the shadow region 176 depends on the position of the 2D array 170 and the 2D array 170, with respect to the interventional device 174, and the geometry of the beams used to acquire the ROI 172. Moving the interventional device 174 with respect to the 2D array 170 or adjusting the geometry of the beams used to acquire the ROI 172 may result in a different shadow region.

Referring to FIGS. 1, 2, and 3, at step 202, the processor 116 controls the probe 106 to acquire ultrasound data of a region-of interest, such as the region of interest (ROI) 152. According to an embodiment, an interventional device, such as the interventional device 150 is included in the ROI 152. The interventional device 150 may be a catheter according to an exemplary embodiment. However, other types of interventional devices, including stents or any other object placed within a patient's body may be used according to other embodiments. Next, at step 204, the processor 116 identifies the position of the interventional device 152 with respect to the probe 106.

Many different techniques may be used to identify the position of the interventional device 150 with respect to the probe 106. For example, according to an exemplary embodiment, the processor 116 may apply an image processing algorithm to the ultrasound data acquired at step 202 in order to detect the position of the interventional device 150. The image processing algorithm may be applied either to raw ultrasound data or to ultrasound data that has been scan converted. According to an embodiment where raw ultrasound data is used, the processor 116 may scan convert the ultrasound data as part of the image processing algorithm. Many different image processing algorithms may be used to identify the interventional device based on the ultrasound data. An embodiment will be described where the image processing algorithm is used to identify the position of a catheter. It should be appreciated that it is not necessary to have the tracking device 151 attached to the interventional device 150 for embodiments that use an image processing algorithm to identify the position of the interventional device 150. For purposes of this disclosure, it should be appreciated that the term "position" is defined to include both the translational position of the interventional device 150 as well as the orientation, which could include rotations about any one or more arbitrary axes.

However, according to other embodiments, the tracking device 151 may be used to determine the position of the interventional device 150. The tracking device 151 may be a component in an electromagnetic tracking system. For example, the tracking device may include three mutually orthogonal coils adapted to detect the strength of a magnetic field generated by a nearby field generator (not shown). The tracking receiver 117 (shown in FIG. 1) receives signals from the tracking device 151 and, based on the signals from each of the three orthogonal coils, the real-time position of the interventional device 150 may be calculated. Other types of tracking devices may also be used. For example, the tracking device 151 may include one or more accelerometers or gyroscopic sensors in order to effectively track the position of the interventional device 150. If the clinician inputs a starting position for the interventional device, such as by positioning it in a specific localization position, then the combination of gyroscopic sensors and accelerometers may detect accelerations in both linear directions and rotational directions. Since the initial position of the interventional device is known, the processor 116 may calculate the real-time position of the interventional device by integrating signals from the accelerometers and gyroscopic sensors. Any other type of tracking device capable of determining the position of the interventional device 150 may be used according to additional embodiments. According to another embodiment, the tracking device may include a transducer element mounted on the interventional device. The transducer element may be configured to emit ultrasound energy at a frequency that is detectable by the probe 106. The processor 116 may use the signals from the transducer element to localize the interventional device. The transducer element would need to transmit ultrasound energy at a frequency that is within the bandwidth of the probe 106. However, in order to avoid disrupting the ultrasound data, it would be necessary to pulse the transducer element located on the interventional device.

According to another embodiment, the processor 116 may threshold and segment the ultrasound data in order to identify the position of the interventional device 150. Pixels/voxels showing the interventional device should be very bright in intensity with respect to the rest of the ultrasound data. The processor 116 may, for example, apply a connected component analysis to identify all pixels or voxels that should be labeled as part of the interventional device 150. Catheters tend to be generally cylindrical in shape. Therefore, some embodiments may apply a shape-based image processing algorithm. For example, the processor 116 may search for a connected group of pixels or voxels that have a size and shape consistent with a catheter or other interventional device. Other embodiments may fit a deformable model, such as a tube-like mesh structure, to the ultrasound data in order to identify the interventional device. The processor 116 may have access to the specific size and shape of the interventional device. For example, the user may enter the type of interventional device 150 being used before acquiring the ultrasound data at step 200 or the processor 116 may automatically detect the type of interventional device through an RFID chip or other identification technique. If the processor 116 has a priori knowledge about the size and shape of the interventional device 150, the processor 116 should be able to more accurately identify the exact position of the interventional device based on the ultrasound data. According to an embodiment, the processor 116 may combine techniques and first perform a thresholding operation and then match the thresholded region or volume to a model of the interventional device. This technique may provide additional accuracy and precision compared to a technique using only thresholding. The previously mentioned image processing techniques are well-known by those skilled in the art and will therefore not be described in additional detail. It should be appreciated that many different image processing algorithms and techniques may be used at step 204 according to other embodiments.

Next, at step 206 the processor 116 identifies a shadow region 154 caused by the position of the interventional device 150 with respect to the probe 106. For purposes of this disclosure, the term "shadow region" is defined to include a region or volume where the ultrasound data may be compromised due to the scattering, reflecting or otherwise blocking of acoustic energy from the probe 106. For example, in FIG. 3, the shadow region 154 is located on the distal side of the interventional device 150 with respect to the probe 106. According to an embodiment, the processor 116 may calculate the extent of the shadow region 154 by calculating which of the acquired lines of ultrasound data would intersect the interventional device 150 based on the position and shape of the interventional device 150 and the acquisition geometry. The acquisition geometry includes the relative position of the probe 105 with respect to the interventional device and the type of acquisition being performed. FIG. 3 includes a first dashed line 156 and a second dashed line 158. The first dashed line 156 and the second dashed line 158 represent lines along which ultrasound data are acquired. The first and second dashed lines 156, 158 represent the boundaries of the shadow region 154 shown in FIG. 3. The interventional device 150 reflects or scatters the acoustic energy transmitted by the probe 106 in to the ROI 152. At step 206 the processor 116 also identifies a non-shadow region 160. The non-shadow region 160 includes all of the ROI other than the shadow region 154. The processor 116 may not specifically perform an additional step of identifying the non-shadow region 160 according to some embodiments. However, since the non-shadow region 160 includes all of the ROI other than the shadow region 154, by positively identifying the shadow region 154, the processor 116 has in effect also identified the non-shadow region 160. Those skilled in the art will also appreciate that the non-shadow region 160 includes the region 162 that is located between the probe 106 and the interventional device 150.

Next, at step 208, the processor 116 identifies a first subset of the ultrasound data that was acquired from the shadow region 154 and a second subset of the ultrasound data that was acquired from the non-shadow region 160. According to one embodiment, step 208 may include identifying which of the voxels or pixels were acquired from the shadow region 154 and which of the voxels or pixels were acquired from the non-shadow region 160. Since the ultrasound data was acquired by the probe 106 and the shadow region 154 is defined with respect to the probe, it is computationally easy for the processor 116 to identify the first subset of the ultrasound data and the second subset of the ultrasound data.

At step 210, the processor 116 generates an image from the ultrasound data. In the process of generating the image, the processor 116 visualizes the first subset of the ultrasound data differently than the second subset of the ultrasound data.

Next, at step 212, the processor 116 displays the image on the display device 118. As described previously with respect to step 210, it may be desirable to visualize the first subset of the ultrasound data in a manner that allows the clinician to easily distinguish the portion of the image generated from the first subset of the ultrasound data from the portion of the image generated from the second subset of the ultrasound data. This would allow the clinician to quickly and easily determine if the portion of the image represents data from the shadow region 154 or data from the non-shadow region 160.

Figure 5:
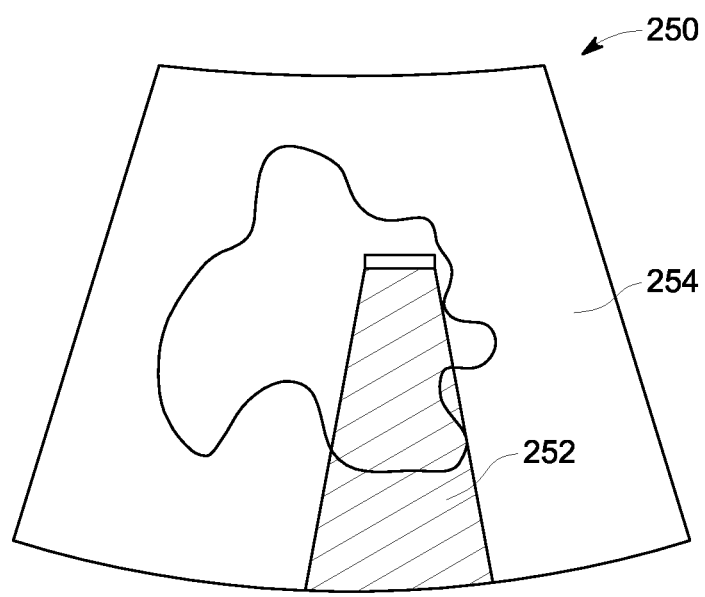
FIG. 5 is a schematic representation of an image generated from ultrasound data according to an embodiment.

FIG. 5 is a schematic representation of an image 250 generated from ultrasound data according to an embodiment. The image 250 may have been generated from 2D data, such as that represented by the ROI 152 shown in FIG. 3, or the image 250 may have been generated from 3D data, such as that represented by the ROI 172 shown in FIG. 4. For example, the image 250 may represent a slice or cut-plane generated from 3D data. According to other embodiments, the image may be a volume-rendered image or a surface-rendered image generated from 3D data.

Still referring to FIG. 5, a shadow image area 252, represented by the hatching, is generated based on ultrasound data acquired from the shadow region 154 (shown in FIG. 3) while non-shadow image area 254 is generated based on ultrasound data acquired from the non-shadow region 160 (shown in FIG. 3). In some types of images, such as 2D images acquired with a 2D probe or slice generated from 3D data, the shadow image area 252 may directly correspond with the shadow region 154 (shown in FIG. 3). In other words, the shape and orientation of the shadow image area 252 may be the same as the shadow region 154. However, in other types of images, such as volume-renderings, the shadow image area 252 may not directly correspond with the shadow region 176 (shown in FIG. 4). Instead, the shadow image area 252 may indicate that data from one or more voxels was acquired from within the shadow region 176 (shown in FIG. 4).

As discussed previously, many different techniques may be used to visualize the first subset of the ultrasound data differently from the second subset of the ultrasound data. Visualizing the first subset of ultrasound data differently from the second subset of the ultrasound data will then allow the clinician to easily identify whether a particular portion of the image is part of the shadow image area 252 or the non-shadow image area 254. The first subset of the ultrasound data that was acquired from the shadow region 154 (shown in FIG. 3) may be visualized with one or more different visualization parameters than the second subset of the ultrasound data that was acquired from the non-shadow region 160 (shown in FIG. 3). Visualization parameters that may be used to visualize the first subset of the ultrasound data differently than the second subset of the ultrasound data include color, transparency, and brightness. An exemplary way of applying different visualization parameters will be described below with respect to 3D ultrasound data according to an exemplary embodiment.

In a 3D ultrasound dataset, each voxel, or volume element, is assigned one or more values based on the received ultrasound data. The processor 116 (shown in FIG. 1) or a separate volume-rendering unit (not show) then converts the voxel data into a format for display. The exact conversion process used by the processor 116 depends on the type of image being generated. For example, the processor 116 may generate images including slices of arbitrary cut planes, volume-rendered images, and projection images. It should be appreciated that the processor 116 may also generate other types of images from the data. In order to visualize the ultrasound data, the processor 116 associates values for one or more visualization parameters with each voxel. For example, the processor may use one or more mapping functions to associate visualization parameters, such as transparency, intensity, and color, with each voxel. However, according to an embodiment, the first subset of the ultrasound data is visualized differently than the second subset of the ultrasound data. The processor 116 may visualize the first subset of the ultrasound data and the second subset of the ultrasound data using different transparencies, intensities, or different colors. Or according to an embodiment, the colors may be modulated differently. The processor 116 may alter any other visualization parameter that would allow the clinician to distinguish the shadow image area 252 from the non-shadow image area 254. Hereinafter, the effects of visualizing the first subset of the ultrasound data differently from the second subset of the ultrasound data will be described with respect to way that they alter the appearance of the image with respect to FIG. 5. Additionally, as a convention, the differences in visualization will be described in terms of how they change the appearance of the image. The visualization techniques used to achieve the effects described below are familiar and well-known to those skilled in the art.

Referring now to FIG. 5, the shadow image area 252 may be displayed with a different transparency than the non-shadow image area 254. For example, the shadow image area 252 may be visualized with a greater level of transparency than the non-shadow image area 254. The clinician would then be able to easily identify the shadow-image area 252 due to the increased transparency of the area with respect to the non-shadow image area. According to another embodiment, all the voxels acquired from the shadow region may be visualized as fully transparent, resulting in the display of no data in the shadow image area 252. According to another embodiment, the color or colors used in the display of the shadow image area 252 may be modulated differently with respect to the non-shadow image area 254. For example, if all the colors in the shadow image area 252 are modulated differently with respect to the non-shadow image area 254, it would be easy for the clinician to identify the shadow image area 252. The colors may be modulated so that the colors in the shadow image area 252 are warmer, cooler, red-shifted, or blue-shifted with respect to the non-shadow image area 254. Other types of color modulation may also be used. According to yet other embodiments, the shadow image area 252 may be visualized using different intensity than the non-shadow image area 254. The shadow image area 252 may be visualized with either greater intensity or a lower intensity than the non-shadow image area 254. The differences in visualization may be used in order to highlight the shadow image area 252 with respect to the non-shadow image area 254, or the differences in visualization may be used in order to de-emphasize the shadow image area 252. According to another embodiment, the shadow image area 252 may be visualized differently from the non-shadow image area 254 according to two or more visualization parameters. For example, visualization parameters, such as intensity, color, and transparency, may be modulated in combination in order to more clearly distinguish the shadow image area 252 from the non-shadow image area 254.

According to another embodiment, the processor 116 (shown in FIG. 1) may visually distinguish the shadow image area 252 according to other techniques. For example, the processor 116 may outline the shadow image area 252 in order to delineate it from the non-shadow image area 254. According to another embodiment a geometric solid in the shape and location of the shadow region may be generated as part of a volume-rendered image. This way, when viewing a volume-rendered image from different perspectives, the clinician may still easily locate the geometric solid and know that image within the geometric solid is less reliable since it was acquired from within the shadow region 176 (see FIG. 4) of the interventional device 174 (see FIG. 4).

Figure 6:
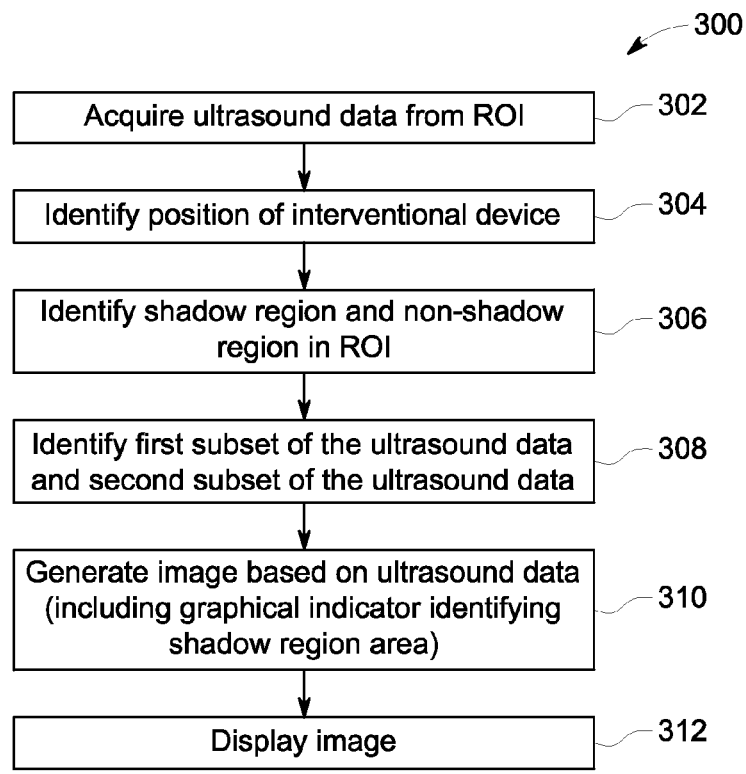
FIG. 6 is a flow chart of a method in accordance with an embodiment.

FIG. 6 is a flow chart of a method 300 in accordance with an exemplary embodiment. The individual blocks of the flow chart represent steps that may be performed in accordance with the method 300. Additional embodiments may perform the steps shown in a different sequence and/or additional embodiments may include additional steps not shown in FIG. 6. The technical effect of the method 300 is the identification of a shadow region and a non-shadow region in an ROI and the display of an image including a graphical indicator identifying a shadow region area. Step 302 is identical to step 202 (shown in FIG. 2), step 304 is identical to step 204 (shown in FIG. 2), step 306 is identical to step 206 (shown in FIG. 2), and step 308 is identical to step 208 (shown in FIG. 2). Since steps 302, 304, 306, and 308 were previously described with respect to FIG. 2, they will not be described again with respect to the method 300 shown in FIG. 6. Steps 310 and 312 will be described according to an embodiment where the method 300 is implemented using the ultrasound imaging system 100 (shown in FIG. 1).

At step 308, the processor 116 had identified a first subset of the ultrasound data that was acquired from the shadow region and a second subset of the ultrasound data that was acquired from a non-shadow region. During step 310, the processor 116 generates an image based on the ultrasound data. According to an embodiment, the image includes a shadow region area that was generated at least in part based on the first subset of the ultrasound data. Since the first subset of the ultrasound data was acquired from a shadow region, such as the shadow region 176 shown in FIG. 4, the shadow region area is generated based on data acquired from the shadow region 176. The processor 116 may also generate a graphical indicator as part of the image. The graphical indicator identifies the shadow region area in the image, thus making it easier for the clinician to determine the reliability of different portions of the image. The graphical indicator may include any type of technique used to visually indicate the shadow region area so that a clinician can distinguish the shadow region area from a non-shadow region area that is generated from data acquires outside the shadow region 176. Examples of graphical indicators include visualization techniques, such as those described with respect to the method 200, as well as other techniques such as outlining or generating a geometric solid in the shape of the shadow region.

Figure 7:
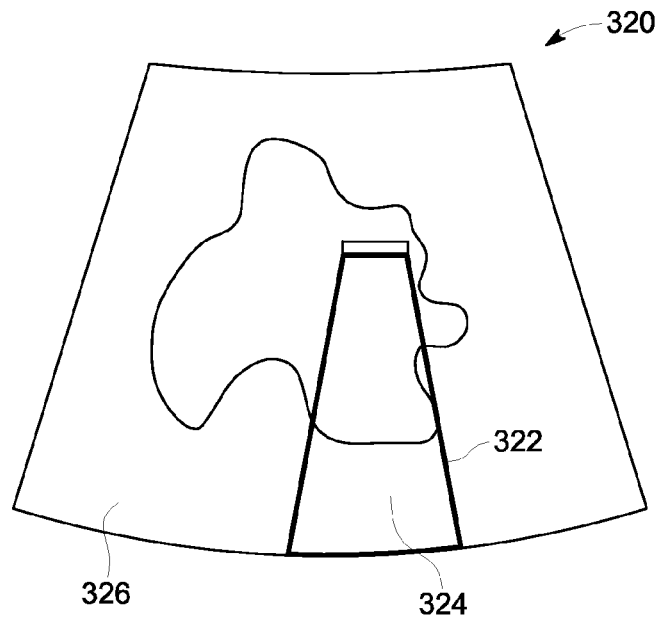
FIG. 7 is a schematic representation of an image in accordance with an embodiment.

FIG. 7 is a schematic representation of an image 320 in accordance with an embodiment. The image 320 includes an outline 322 separating a shadow region area 324 of the image 320 from a non-shadow region area 326 of the image 320. The outline 322 may be configured differently according to other embodiments.

Figure 8:
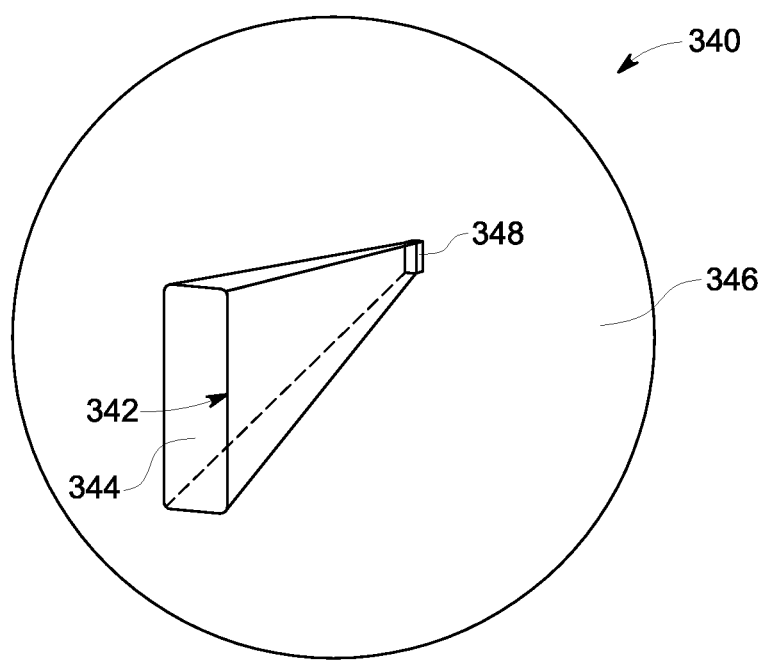
FIG. 8 is a schematic representation of an image in accordance with an embodiment.

FIG. 8 is a schematic representation of an image 340 in accordance with an embodiment. The image 340 is a volume-rendered image according to an embodiment. The image 340 includes a geometric solid 342 that delineates a shadow region area 344 from a non-shadow region area 346. The geometric solid 342 is a representation of the size and shape of a shadow region caused by the position of an interventional device 348. The shape of the geometric solid 342 may depend upon the shape of the interventional device 348 and the position and geometry of the probe used to acquire the data. The geometric solid 342 shown in FIG. 8 is a rendering of the shape of the shadow region. The geometric solid 342 may be superimposed over the shadow region area 344 as is shown in FIG. 8, or the geometric solid 342 may replace the replace the ultrasound data in the shadow region area according to other embodiments. The geometric solid 342 may be rotated or adjusted in synchronization with the rest of the image in order to show different views of the image or cut-planes. According to an embodiment, the processor 116 may be configured to toggle between displaying the graphical indicator, such as the geometric solid 342 or the outline 322, and displaying the image without the graphical indicator. For example, the clinician may be able to alternate between viewing the image including the graphical indicator and viewing the image without the graphical indicator based on a input from the user interface 115.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
    acquiring ultrasound data with a probe of a region-of-interest, the region-of-interest including an interventional device;
    automatically identifying a position of the interventional device with respect to the probe;
    automatically identifying within the region-of-interest a shadow region based on the position of the interventional device with respect to the probe;
    automatically identifying a subset of the ultrasound data that was acquired from the shadow region;
    generating an image based on the ultrasound data, the image including a graphical indicator identifying a shadow image area generated from the subset of the ultrasound data; and
    displaying the image.

2. The method of claim 1, wherein the graphical indicator comprises an outline.

3. The method of claim 1, wherein the image comprises a volume-rendered image and the graphical indicator comprises a geometric solid in the shape of the shadow region.

4. The method of claim 1, further comprising toggling between displaying the graphical indicator and removing the graphical indicator in response to a user input.

5. The method of claim 1, wherein the graphical indicator comprises colorizing the shadow image area.

6. The method of claim 1, wherein the graphical indicator comprises applying a different transparency to the shadow image area.

7. A method of ultrasound imaging comprising:
    acquiring ultrasound data with a probe of a region-of-interest, the region-of-interest including an interventional device;
    automatically identifying a position of the interventional device with respect to the probe;
    automatically identifying within the region-of-interest a shadow region and a non-shadow region based on the position of the interventional device with respect to the probe;
    automatically identifying a first subset of the ultrasound data that was acquired from the shadow region and a second subset of the ultrasound data that was acquired from the non-shadow region;
    visualizing the first subset of the ultrasound data differently than the second subset of the ultrasound data to generate an image; and
    displaying the image.

8. The method of ultrasound imaging of claim 7, wherein the first subset of the ultrasound data is visualized with a different color than the second subset of the ultrasound data.

9. The method of ultrasound imaging of claim 7, wherein the first subset of the ultrasound data is visualized with a different transparency than the second subset of the ultrasound data.

10. The method of ultrasound imaging of claim 9, wherein the first subset of the ultrasound data is visualized with a greater level of transparency than the second subset of the ultrasound data.

11. The method of ultrasound imaging of claim 9, wherein first subset of the ultrasound data is visualized as fully transparent.

12. The method of claim 7, wherein the first subset of the ultrasound data is visualized with both a different color and a different transparency than the second subset of the ultrasound data.

13. The method of claim 7, wherein the first subset of the ultrasound data is visualized with a different intensity than the second subset of the ultrasound data.

14. The method of ultrasound imaging of claim 7, wherein said automatically identifying the position of the interventional device comprises implementing an image processing algorithm on raw ultrasound data.

15. The method of ultrasound imaging of claim 7, wherein said automatically identifying the position of the interventional device comprises receiving signals from a tracking device located on the interventional device.

16. An ultrasound imaging system comprising:
    a probe;
    a display device; and
    a processor in electronic communication with the probe and the display device, wherein the processor is configured to:
        control the probe to acquire ultrasound data of a region-of-interest including an interventional device;
        identify a position of the interventional device with respect to the probe;
        identify a shadow region in the region-of-interest caused by the interventional device based on the position of the interventional device with respect to the probe;
        identify a non-shadow region in the region-of-interest;
        identify a first subset of the ultrasound data that was acquired from the shadow region and a second subset of the ultrasound data that was acquired from the non-shadow region;
        generate an image by visualizing the first subset of the ultrasound data differently than the second subset of the ultrasound data; and
        display the image on the display device.

17. The ultrasound imaging system of claim 16, further comprising a tracking device attached to the interventional device.

18. The ultrasound imaging system of claim 17, wherein the tracking device comprises a component of an electromagnetic tracking system.

19. The ultrasound imaging system of claim 17, wherein the tracking device comprises a transducer element positioned on the interventional device.

20. The ultrasound imaging system of claim 17, wherein the processor is configured to visualize the first subset of the ultrasound data with a different color than the second subset of the ultrasound data.

21. The ultrasound imaging system of claim 17, wherein the processor is configured to visualize the first subset of the ultrasound data with a different transparency than the second subset of the ultrasound data.

* * * * *